United States Patent [19]

Barrett

[11] Patent Number: 4,555,177

[45] Date of Patent: Nov. 26, 1985

[54] METHOD AND APPARATUS FOR DETECTING SINGLET STATE RESONANCE FLUORESCENCE

[75] Inventor: Terence W. Barrett, Bethesda, Md.

[73] Assignee: The United States of America as represented by the Secretary of the Navy, Washington, D.C.

[21] Appl. No.: 564,583

[22] Filed: Dec. 22, 1983

[51] Int. Cl.[4] ........................................ G01N 21/64
[52] U.S. Cl. ............................ 356/318; 250/458.1; 250/459.1; 356/367
[58] Field of Search ............... 356/317, 318, 417, 364, 356/367; 350/458.1, 459.1, 461.1, 461.2

[56] References Cited

U.S. PATENT DOCUMENTS 3,897,155 7/1975 Smythe .
4,031,399 6/1977 Klein et al. .
4,203,670 5/1980 Bromberg ............................ 356/367
4,299,486 11/1981 Nogami et al. ...................... 356/318

OTHER PUBLICATIONS

Barrett et al. "Detection of Triplet States in a Laser Dye from Linear and Circular Polarization Studies"; Applied Optics, vol. 22, p. 2522, Sep. 1, 1983.

Primary Examiner—F. L. Evans
Attorney, Agent, or Firm—Robert F. Beers; William T. Ellis; William R. Sharp

[57] ABSTRACT

A method and apparatus for detecting the wavelength of singlet state resonance fluorescence of a sample, wherein the sample is illuminated sequentially with various incident wavelengths. For each wavelength, linearly polarized and circularly polarized components are allowed to pass sequentially by a first polarizer to the sample. The sample emits light as a result of spontaneous molecular energy transitions. Four components of the emitted light are allowed to sequentially pass to a detector by a second polarizer. The intensities of these components are then detected, and these values can be employed to obtain a new ratio for each wavelength. The wavelength at which this ratio equals one is selected as the wavelength of resonance fluorescence. In one example, a computer is provided to control the illumination of the sample and the two polarizers, and also may be utilized to compute the above ratios.

11 Claims, 7 Drawing Figures

METHOD AND APPARATUS FOR DETECTING SINGLET STATE RESONANCE FLUORESCENCE

BACKGROUND OF THE INVENTION

This invention relates to the fluorescence emission spectra of fluorescing compounds and more particularly to methods for the determination of the wavelength at which pure singlet state resonance fluorescence occurs.

First, some terms used throughout the specification will be discussed and summarily defined.

Consider a system of two electrons in a molecule. Each electron has an associated spin quantum number S, which may be $+\frac{1}{2}$ or $-\frac{1}{2}$. By the Pauli exclusion principle, two electrons occupying the same orbital must have their spins opposed. The projection of the spin quantum number for more than one electron is generally denoted by M. For the above mentioned state, therefore, M=O; this state being referred to as the singlet state. However, when one of the electrons is promoted to an upper orbital, its spin may be oriented in the same or in the opposite direction to that of the electron remaining in the original orbital. Therefore, in this state, M may equal $+1$, $0$, or $-1$. This state is referred to as the triplet state.

As noted above, the invention described herein relates to the determination of the wavelength of singlet state resonance fluorescence, a term which will now be defined.

When a molecule is exposed to exciting radiation, singlet or triplet states may be promoted to excited singlet or triplet states. Spontaneous transitions from these excited states to unexcited states gives rise to light emission. Thus, in a compound having singlet and triplet states, an emission spectra will be obtained which results from both singlet to singlet, singlet to triplet, and triplet to triplet conversions or transitions. However, at a certain wavelength for a particular compound, absorption and emission of radiation will involve only singlet to singlet transitions. The wavelength at which the above mentioned transition occurs is called singlet state resonance fluorescence. At this wavelength, there are only singlet emissions, and no triplet emissions resulting from singlet-triplet conversion.

There has been intense interest in developing methods of determining the wavelength at which resonance fluorescence occurs. By means of such methods, several results are achieved.

First, the most efficient lasing line for pumping lasing dyes can be detected. Triplet states in a laser dye have considerable absorption for the laser light so that absorption of photons by the triplet states causes laser loss. Additionally, only singlet to singlet transitions are responsible for stimulating emission in the dye. Thus, excitation of triplet states in the laser dye excludes electrons with such excitations from the lasing process. Accordingly, using a wavelength at which resonance fluorescence occurs in a dye laser, wherein only singlet to singlet transitions occur, and singlet-triplet, and triplet-triplet transitions do not occur, considerably increases laser efficiency.

Second, two photon coherent states may be produced from resonance fluorescence. These are light pulses whose degrees of second-order coherence violates various inequalities thought to hold in the classical theory of light. The pulses obtained are also anti-bunched, which is light that violates the single beam inequality.

Third, a knowledge of the wavelength for resonance fluorescence permits optical bistability. Changing from singlet to triplet conditions results in bistability (atomic cooperation and resonance fluorescence). At resonance, with cavity damping larger than atomic relaxation, and incident field decreased, the approach to the one atom stationary state is monotonic and the system exhibits hysteresis.

Presently several experimental techniques have been developed to determine the quantum yield of triplet formation from the first excited singlet level. When the wavelength is detected where there is no yield of triplet formation, only singlet-singlet transitions are possible. Thus, the wavelength for resonance fluorescence is detected.

One method involves the addition of various heavy atom solvents to a lasing dye solution, which are known to either increase or decrease the rate constant for triplet formation. This method is indirect in that it infers triplet enhancement, or decrease, by measuring a change in the singlet fluorescence yield. This method is described in detail in Shafer, F. P., ed. *Topics in Applied Physics: Dye Lasers.*, N. Y. Springer-Verlag, 1973, pp. 155–156. However, this method along with the other methods, is quite insensitive, and is highly time consuming and laborious to carry out.

SUMMARY OF THE INVENTION

Accordingly, it is an object of the present invention to provide a method of detecting the wavelength for singlet state resonance fluorescence that is highly sensitive and accurate.

It is also an object of this invention to provide a method of detecting the wavelength for resonance fluorescence that is relatively easy and quick to perform.

The above objects are realized in a method and apparatus in which the sample is illuminated with incident light of different polarizations. In the method, the sample is illuminated sequentially with light of different wavelengths. At each wavelength, the sample is sequentially illuminated with different components of the incident light. These components include a linearly polarized component and a circularly polarized component. In response to the incident light, the sample emits light spontaneously as a result of molecular energy transitions. For each wavelength of the incident light, intensities of components of the emitted light are sequentially detected. The components of the emitted light include a linearly polarized emitted component, resulting from the incident linearly polarized component, and a circularly polarized emitted component resulting from the incident circularly polarized component. The wavelength is then selected at which the intensity of the circularly polarized emitted component equals zero and where the intensity of the linearly polarized emitted component has some value. The selected wavelength is the wavelength for resonance fluorescence.

The apparatus for performing the above method includes a polarizer for selectively passing only certain polarized components of the incident light and a polarizer for performing the same function in respect to the emitted light. In the preferred embodiment, a control means, such as a computer, may be provided to control the two polarizers and analyze the detected emitted component intensities.

The above described method is very quick and easy to perform, since it requires only a few intensity readings, and is also highly accurate.

DESCRIPTION OF THE PREFERRED EMBODIMENTS

An apparatus and method is described herein for detecting the wavelength of singlet state resonance fluorescence for a sample, wherein the sample is illuminated with different polarizations of incident light. Different polarizations of the emitted light are detected to determine the wavelength for resonance fluorescence.

Figure 1:
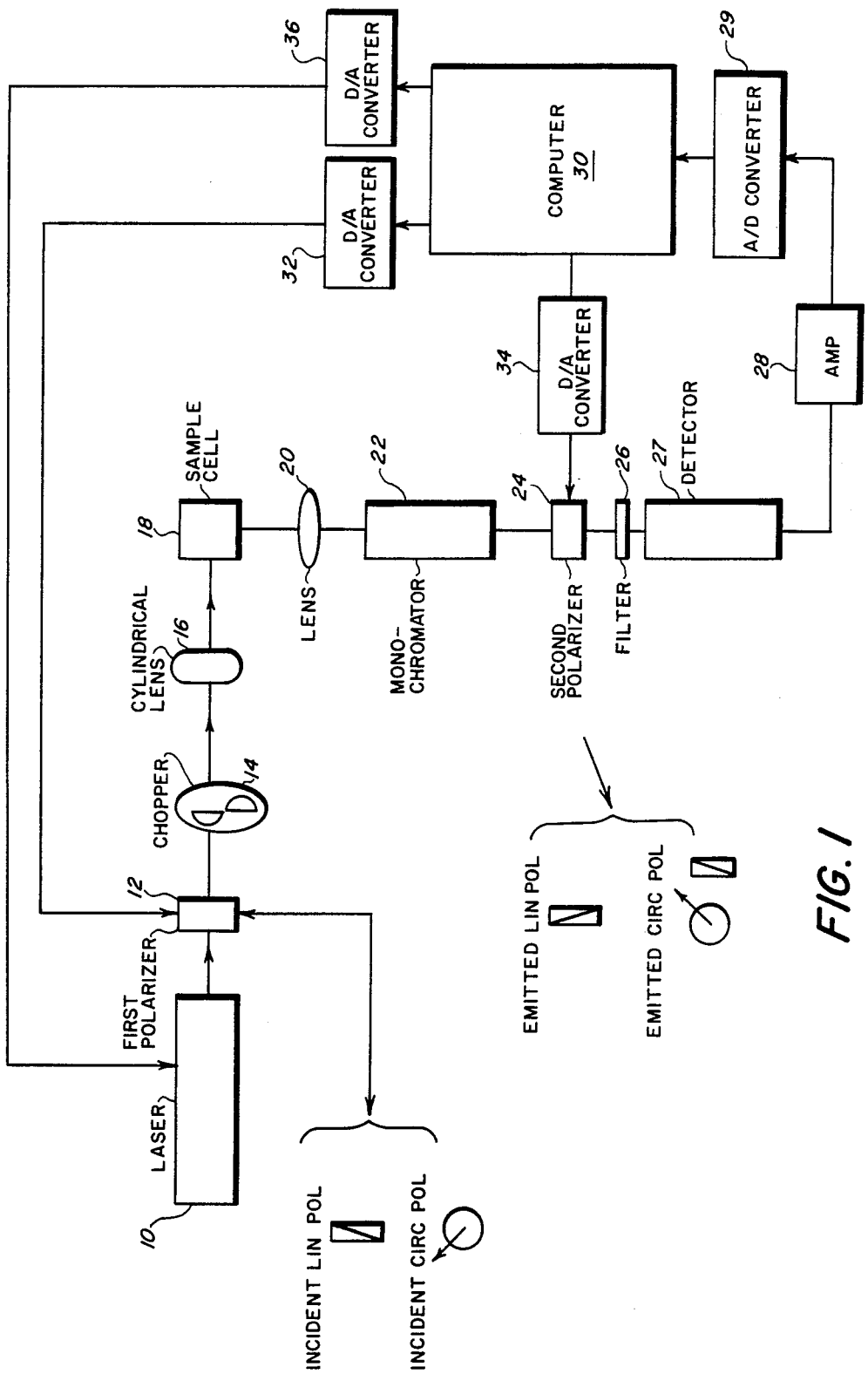
FIG. 1 shows a schematic representation of the apparatus for performing the method of detecting the wavelength for resonance fluorescence of a sample.

Referring now to FIG. 1, a schematic representation of an apparatus for performing the above method is shown. Laser 10 provides incident light for illuminating a sample, as will be described herein below, which may be, by way of example, a scanning dye laser pumped by a gas (i.e., Krypton or Argon) laser. Most importantly, however, laser 10 should preferably be capable of scanning over a wide range of wavelengths, for example 300–700 nm, the significance of which will become apparent in the description of the operation of the device, later described. For the sake of clarity, light from laser 10 before reaching the sample will be hereafter referred to as incident light, and light emitted by the sample will be referred to as emitted light.

Incident light from laser 10 then passes through a first polarizer 12 for selectively passing certain circularly or linearly polarized components of light from laser 10. Preferably, first polarizer 12 is a piezoelectric type polarizer, typically referred to as a Pockel's Cell, which comprises a piezoelectric plate. This plate may be, by way of example, potassium dihydrogen phosphate or ADP, KDP ($KH_2PO_4$), KDA ($KH_2AsO_4$), or any substance exhibiting electrically controllable double refraction. An electrical signal may be applied by means of electrodes attached to the plate, as described in more detail below, to create an electric field across the crystal. This electric field causes distortions in the crystal leading to linear or circular polarizing effects, depending on the signal applied. A piezoelectric polarizer as described above is commercially available from Karl Lambrecht & Co. of Chicago, Ill.

As shown, a mechanical chopper 14 is provided in the illustrated embodiment, which comprises a rotating disc having two apertures. The rotation of chopper 14 causes a periodic cut-off of incident light, and thus a corresponding effect as to emitted light. Thus, in the detection of emitted light intensities, discussed in more detail below, a periodic zero reading is detected. This zero reading provides a zero "baseline", or a good reference in detecting the emitted intensities absolute amplitude. It is emphasized, however, that this feature is purely optional, and is not critical to the operation of the device shown in FIG. 1. Incident light from chopper 14 then passes to cylindrical lens 16, which acts to focus the light onto sample cell 18.

Sample cell 18 comprises a four sided container preferably of fused quartz, sometimes referred to as an FQ cell. The sample being analyzed is contained by cell 18 such that light from lens 16 passes into the sample. Preferably, one side of cell 18 is positioned so as to be perpendicular to the optical path of the incident light, and another side is oriented so as to be perpendicular to the optical path of sample emitted light. This cell orientation causes a minimum of undesirable refraction effects. An FQ cell as described above is commercially available from Fisher Chemical Company of Pittsburgh, Pa.

Sample cell 18 need not be of any particular shape, and other optically inactive materials other than quartz (i.e., silica) are equally suitable. The FQ cell described above, however, is easily obtainable from many commercial sources in addition to the one mentioned.

Light incident on sample cell 18 causes excitation of sample molecules to excited energy levels. Spontaneous transitions down to lower energy levels then typically occur, causing light to be emitted by the sample at right angles to the incident light and other angles.

Emitted light passes through lens 20, which focuses the light onto monochromator 22. Monochromator 22, which is conventional in nature and well known to those skilled in the art, acts to pass only a desired wavelength of emitted light to second polarizer 24. Monochromator 22 is provided as a preferred feature, because in analyzing sample laser dyes, this feature permits an emission spectrum to be obtained for a variety of emitted light wavelengths. Thus, valuable information as to the wavelength scanning capability of the sample dye under analysis may be obtained. It is emphasized, however, that monochromator 22 is optional, such that in an alternative arrangement, this feature might be omitted. Accordingly, all wavelengths of emitted light would be directed onto second polarizer 24. The ratio X, described below, may be equally well determined with this arrangement.

Second polarizer 24 is similar to first polarizer 12, and thus is preferably of the piezoelectric type. However, polarizer 24 includes two piezoelectric plates. Second polarizer 24 may selectively pass certain circularly or linearly polarized components of light emitted from the sample. The selected emitted polarized component then passes through a suitable filter 26, for excluding stray light, to a detector 27 which may be, for example, a photomultiplier. Detector 27 detects intensities of emitted light components, and produces an electrical signal that is proportional to light intensity. This signal is passed to amplifier 28, which sends an amplified signal to A/D (analog to digital) converter 29. A/D converter 29 then converts its input into a digital signal, which is coupled into computer 30. The digital signal received by computer 30 is analyzed as will be later described. Computer 30 acts to control the polarizations of polarizers 12 and 24, and the output wavelengths of laser 10 as follows.

First, as to the control of polarizers 12 and 24, digital signals from computer 30 are coupled into D/A converters 32 and 34, which produce analog outputs. These outputs are received by first polarizer 12 and second polarizer 24. Polarizers 12 and 24 change in their polarizing effects by means of different voltages applied to the polarizer piezoelectric plates which result from various corresponding digital signals from computer 30.

This varying polarizing effect of the piezoelectric plates of polarizers 12 and 24 via varying applied voltages is known as Pockel's effect, and can be best be understood by considering light to be composed of two contrarotating vectorial components. When these two components are in phase, the light is linearly polarized, and when the two components are 90 degrees out of phase, circular polarization results. The piezoelectric plates of polarizers 12 and 24 act as optical retarders, wherein the phase relation of the vectorial components can be controlled by means of the applied voltages. The retardance of the piezoelectric plate of each polarizer is proportional to the applied voltage, and is given by:

$$\Delta\epsilon = 2\pi n_o^3 r_{63} V/\lambda_o,$$

where $r_{63}$ is the electro-optic constant in m/V, $n_o$ is the ordinary index of refraction, V is the potential difference in volts, and $\lambda_o$ is the wavelength. Therefore, the phase shift retarding effect, and thus the polarizing effect, of each polarizer may be controlled by signals from computer 30 via digital to analog converters 32 and 34.

For illustrative purposes, consider a linearly polarized beam from laser 10 which is incident on polarizer 12. For circular polarization to result, the polarizer must act as a quarter wave plate (90 degrees) so that $n_o^3 r_{63} V/\lambda_o$ must equal $\frac{1}{4}$. The necessary voltage may accordingly be calculated and applied to polarizer 12. A further phase shift of 180 degrees causes an oppositely directed circular polarization, and is obtained by applying a voltage according to the above formula. Similarly, linear polarizations are obtained with applied voltages giving in phase relationships of the vectorial components.

As noted above, polarizer 24 includes two piezoelectric plates. To pass linearly polarized emission components, signals are applied to the plates to make them linear polarizers. To pass circularly polarized components, a signal is applied to one plate to make it act as a quarter wave plate, whereas the second plate is made a linear polarizer. In this way circularly polarized light is linearized by the first plate, which is passed by the second plate.

A table is provided below which gives the electro-optic constants for various piezoelectric materials (at room temperature, and wavelength of 546.1 nm).

| Material | $r_{63}$ (units of $10^{-12}$ m/V) | $n_o$ (approx.) | $V_{\lambda/2}$ (in kV) |
|---|---|---|---|
| ADP (NH$_4$H$_2$PO$_4$) | 8.5 | 1.52 | 9.2 |
| KDP (KH$_2$PO$_4$) | 10.6 | 1.51 | 7.6 |
| KDA (KH$_2$AsO$_4$) | ~13.0 | 1.57 | ~6.2 |
| KD*P (KD$_2$PO$_4$) | ~23.3 | 1.52 | ~3.4 |

As an example, for a 180 degree phase shift (one-half wave) for KDP, the necessary applied voltage is about $7.6 \times 10^3$ V. Necessary voltages for various polarizations can be determined similarly with the above retardance formula.

As to control of laser 10, this is easily accomplished by a microdrive which alters the laser's mirror angles, thus producing different wavelengths of light selected by the mirror angle.

The computer 30 is suitably programmed to act as a control means for laser 10, first polarizer 10, and second polarizer 24 as follows.

First, computer 30 produces appropriate signals as described above, such that laser beam 10 sequentially generates incident laser light of different wavelengths. At each wavelength, signals from the computer 30 are coupled into first polarizer 12, again as explained above, for the purpose of changing the polarizing properties of first polarizer 12. In this regard, computer 30 controls first polarizer 12, such that at each wavelength, first polarizer 12 sequentially passes different incident components of the incident light. These incident components include a first incident component linearly polarized in a direction L, and a second incident component circularly polarized in a direction C. Second polarizer 24 receives the appropriate signals from computer 30, such that for the incident linearly polarized component at a particular wavelength. two components of the light emitted by the sample are allowed to pass in a sequential fashion. These two emitted components include a first emitted component ($I_{\|}$, denoting the intensity of the component) linearly polarized in direction parallel to L, and a second emitted component ($I_{\perp}$) linearly polarized in a direction perpendicular to L. Both the first and second emitted components result from the excitation of the sample by the incident linear component. For the incident circularly polarized component, second polarizer 24 and filter 26 allows two more emitted components to pass in a sequential fashion. These emitted components include a third component ($I_{CO}$) circularly polarized in the same direction (co-rotating) as C, and a fourth emitted component ($I_{CTR}$) circularly polarized in a direction opposite to that of C (contrarotating). The third and fourth emitted components both result from excitation of the sample by the incident circularly polarized component. The four emitted components are then detected by detector 28 that produces a signal proportional to the intensity of each emitted component. The computer is suitably programmed to provide dwell time at each wavelength such that the four emitted components may be detected.

Signals for each emitted component are fed into computer 30. Computer 30 then computes the following new composite ratio X:

$$\frac{(I_{\|} + I_{\perp}) - (I_{CO} + I_{CTR})}{I_{\|} + I_{\perp} + I_{CO} + I_{CTR}}.$$

The computer 30 computes ratio X for each incident wavelength. If for a particular wavelength, X=1, then this wavelength is the wavelength for singlet state resonance fluorescence. The significance of the X value of 1 is explained more fully below.

Pure singlet-singlet emissions are electric dipole allowed. In other words, such emissions result from a spontaneous transition from a high energy singlet state to a low energy singlet state which follows excitation to the high energy singlet state by linearly polarized light. Triplet-triplet emissions are magnetic dipole allowed; such emissions result only from excitation by circularly polarized light. Also, triplet-triplet conversions result only in circularly polarized emissions, and not in linearly polarized emissions. Thus, when incident circularly polarized light falls on a sample, and that sample emits no circularly polarized light, this indicates that no triplet-triplet emissions are present. In other words, $I_{CO}=I_{CTR}=0$. When linearly polarized light is incident on a sample, and that sample emits linearly polarized light, this indicates singlet-singlet emissions. Thus, $I_{\parallel}+I_{\perp}$ has some positive value. Accordingly, for a wavelength at which only singlet-singlet emissions occur, $I_{\parallel}+I_{\perp}$ has a positive value, and $I_{CO}=I_{CTR}=0$. For the above intensity values substituted in the above equation for ratio X gives a value of 1. Thus, for a wavelength at which only pure singlet-singlet emissions occur, the wavelength of singlet state resonance fluorescence, $X=1$.

The computer 30 may be easily adapted to select the wavelength for which $X=1$. As noted above, this wavelength is that for resonance fluorescence. Alternatively, computer 30 may compare the various X values for each incident wavelength, and select the wavelength for which the absolute value of X is closest to one. The wavelength for this value of X would be an approximate wavelength for singlet state resonance fluorescence, where there is a minimum of triplet-triplet or singlet-triplet emissions.

Figure 2:
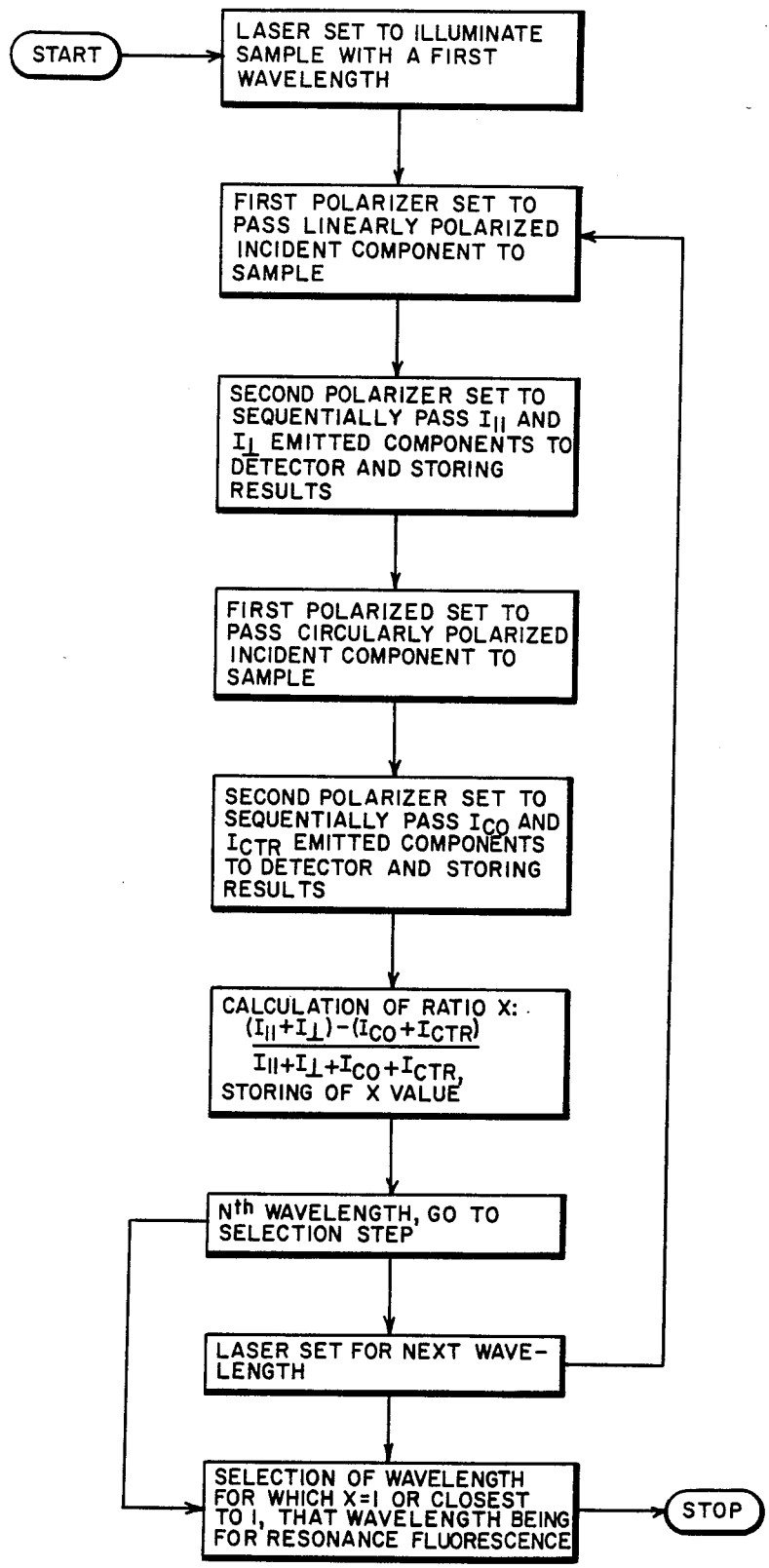
FIG. 2 is a flow chart which indicates the operating procedures of the apparatus of FIG. 1.

Referring now to FIG. 2, there is shown a flow chart of the operating procedures of the apparatus on which the computer program is based, for the case of N different incident wavelengths.

It should be understood that the incident linearly polarized component may be one of several linear polarizations, such as linearly polarized perpendicular or linearly polarized orthogonal. In addition, the incident circularly polarized component may be right or left circularly polarized. The ratio X is dependent on the relation of the emitted component polarizations to the incident component polarizations. Thus, the ratio X may be derived independent of the particular incident polarization directions chosen.

It is emphasized that the wavelength of resonance fluorescence may be determined without the aid of computer 30. Such an alternative embodiment of the invention includes a suitable means for receiving the signal from the detector and for displaying the intensities of emitted components detected. An oscilloscope is one example of such a display means. Control of the laser and polarizers is achieved by manual adjustment by an operator, as discussed in more detail below. Additionally, in such an alternate embodiment, more conventional polarizers other than of the piezoelectric type may be used, although piezoelectric polarizers could also be employed. For example, each polarizer could include a linear polarizing plate of, for example, mica or Polaroid, that can be rotated to obtain different linear polarizations. Each polarizer could also include a conventional quarter wave plate for achieving circular polarizing effects.

In yet another embodiment, computer control of the laser, first polarizer, and second polarizer may be omitted in which case a computer is provided only to receive signals from the detector and compute ratio X.

Although a laser is utilized as an incident light source in the embodiments described above, other light sources may also be used. For example. a mercury arc lamp in conjunction with suitable filters would be an adequate alternative for the generation of sequential incident wavelengths.

In the operation of the apparatus of the illustrated embodiment shown in FIG. 1, the steps performed have been adequately explained above.

In the alternative embodiments referred to above, the wavelength determination is not automatic. The laser is scanned through sequential wavelengths by means of manual operator adjustment. Commercial dye lasers typically have such scanning capability. The electrical signal to the first polarizer may also be varied with suitable means. Or in the case in which the polarizers include linear plates and quarter wave plates, these elements are oriented in a conventional well known fashion to obtain the desired polarizations. Accordingly, for each wavelength, the first polarizer is selectively allowed to pass sequential circular and linear polarization components of the light from the laser 10. Similarly, the second polarizer is allowed to sequentially pass emitted components $I_{\parallel}$, $I_{\perp}$, $I_{CO}$, $I_{CTR}$, described and identified above. Consider the case where the sample is illuminated with circularly polarized light. Here, the quarter wave plate of first polarizer 12 is set to circularly polarize linear light from laser 10. The sample in cell 18 then emits light which is received by second polarizer 24. The quarter wave plate of second polarizer 24 is set such that it linearizes circularly polarized light emitted by the sample. The linear polarizer in polarizer 24 is set either parallel or perpendicular to the incident laser polarization. The parallel component is then a measure of circularly polarized corotating emission, and the perpendicular component a measure of contrarotating emission. These components are sequentially detected by the detector. In the first described alternative embodiment, the detected intensities are monitored by a suitable display means such as an oscilloscope. Thus, the intensities may be read, and ratio X computed for each wavelength. The wavelength for which $X=1$ is then selected as the wavelength of resonance fluorescence. In the second described alternative embodiment, a computer is utilized to compute ratio X.

In the description of the invention thus far, it has been stated that four emitted components, $I_{\parallel}$, $I_{\perp}$, $I_{CO}$, and $I_{CTR}$, are sequentially detected. As noted above, singlet-singlet transitions derive from linearly polarized light and triplet-triplet transitions derive from circularly polarized light. Thus, where there is pure singlet emissions and no triplet emissions, the total intensity of the circularly polarized component of the emitted light will equal zero, and the total intensity of the linearly polarized component of the emitted light will have some positive value. Therefore, $I_{\parallel}+I_{\perp}$ may be considered an emitted linear component and $I_{CO}+I_{CTR}$ may be considered an emitted circular component.

There will now be described a concrete example, wherein a $10^{-5}M$ oxazine/ethanol dye sample is analyzed with an embodiment including an oscilloscope and linear plate-quarter wave plate polarizers. The incident light is derived from Argon ion and Krypton ion lasers. The laser light is polarized by a first polarizer either linearly, for the $I_{\parallel}$ and $I_{\perp}$ measurements, or circularly, for the $I_{CO}$ and $I_{CTR}$ measurements, and chopped by a mechanical chopper at 200 Hz. The beam is then focused by a cylindrical lens into a 1 cm×1 cm FQ sample cell containing the dye solution and the induced fluorescence emissions (either linear or circular) are observed at right angles. The fluorescence emissions are collected by a lens and focused at the entrance slit of a monochromator having a bandwidth of 7.4 nm. The resultant radiation is analyzed either by a linear polarizer (in the case of linear incident excitation) or a counterrotated circular polarizer together with a linear polarizer (in the case of circularly polarized incident excitation). The photodetection is by an RCA photomultiplier (S-I spectral response). The resultant AC electrical signal is then observed on Tektronix 516 oscilloscope. The $I_\parallel$ and $I_\perp$ measurements are obtained by orienting the linear analyzer parallel and perpendicular, respectively, to the linear exciting line. The $I_{CO}$ and $I_{CTR}$ measurements are obtained by first passing the fluorescence emissions through a quarter wave plate which is counterrotated to the quarter wave plate through which the linear exciting line passes. Next. it is sent through the linear analyzer oriented first parallel and then perpendicular, for $I_{CO}$ and $I_{CTR}$ measurements respectively. All four measurements were made as a function of exciting incident wavelength.

Figure 3:
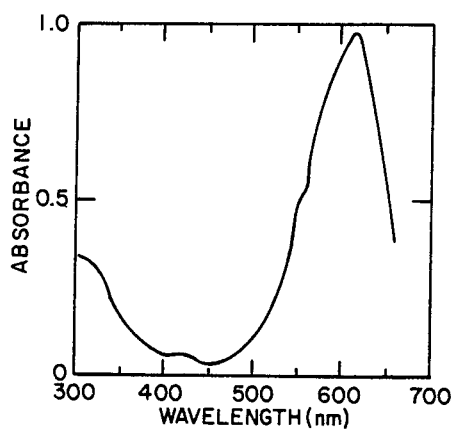
FIG. 3 is a graph showing absorbance versus wavelength for an oxazine/ethanol dye.
Figure 4:
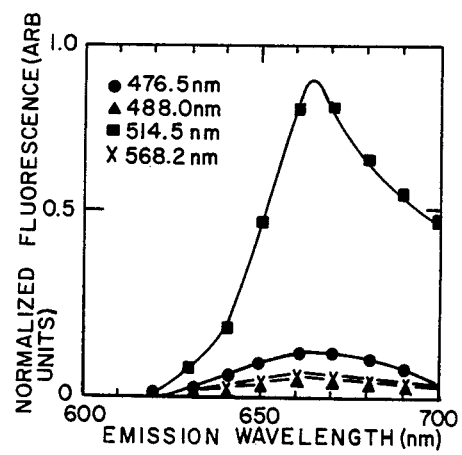
FIG. 4 is a graph showing the fluorescence intensity versus wavelength in an oxazine/ethanol dye.

In FIG. 3 is plotted the spectral absorbance of the oxazine perchlorate in ethanol. The relative fluorescence intensity versus wavelength is shown in FIG. 4 at a number of discrete excitation incident wavelengths: 476.5 nm, 488.0 nm, 514.5 nm and 568.2 nm. The focused laser intensity at the dye cell is approximately 1 W/cm. The relative fluorescence for these emission curves have been corrected for the individual intensities of the laser lines and normalized to the same fluorescence intensity scale. It is noticeable that the emission is most intense at the 514.5 nm excitation as compared with the other incident exciting wavelengths. The relatively weaker fluorescence detected at the other excitation wavelengths is attributed to overlapping triplet-triplet or singlet-triplet absorption states which are simultaneously pumped.

Figure 5:
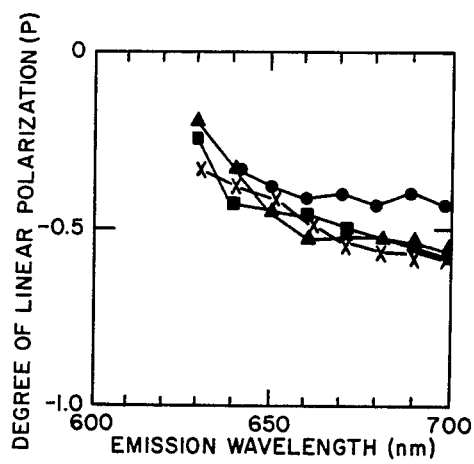
FIG. 5 illustrates in graphical form the degree of linear polarization P, as a function of several incident excitation wavelengths for an oxazine/ethanol dye.

In FIG. 5 is plotted the degree of linear polarization, designated as P, as a function of the several laser incident excitation lines described above. The ratios for all excitation wavelengths are negative. In terms of the classical oscillator model, wherein electrons are considered to be oscillators having discrete frequencies, values of $-\frac{1}{3}$ indicate absorbing and radiating oscillators are at right angles. The obtained measurements are nearer $-\frac{1}{2}$ indicating that the absorbing and radiating oscillators are not completely anisotropic.

Figure 6:
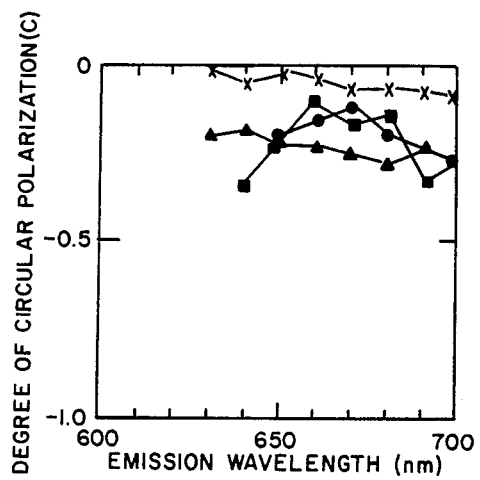
FIG. 6 illustrates in graphical form the degree of circular polarization C as a function of the same incident excitation wavelengths mentioned above in respect to FIG. 4, also for an oxazine/ethanol dye.

In FIG. 6 is plotted the degree of circular polarization, C, as a function of the same laser incident exciting lines. Negative C values indicate the absorbing and fluorescing oscillators are at right angles with a maximum permissible value of $-5/7$. The obtained C values of approximately $-\frac{1}{4}$ indicate that absorbing and fluorescing oscillators are not at exact right angles.

Figure 7:
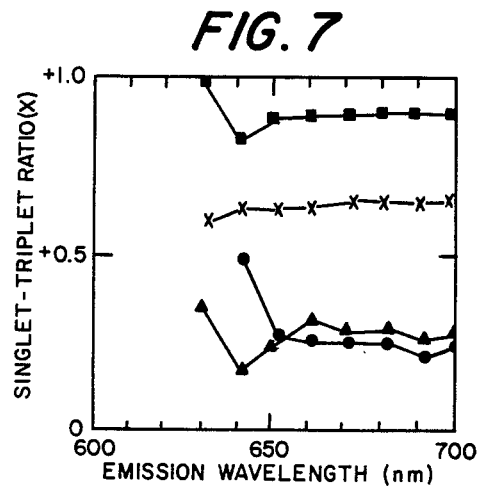
FIG. 7 is a graph showing the ratio X plotted for several incident excitation wavelengths versus emission wavelength, again for an oxazine/ethanol dye.

The new composite ratio, X, is plotted in FIG. 7, showing X versus emission wavelength for various incident wavelengths. In this example, a monochromator has been utilized such that for each incident wavelength, X values are determined for various emission wavelengths. However, as noted previously, use of the monochromator is an optional feature giving insights into the wavelength scanning capability of a sample laser dye. As shown in FIG. 7, the incident wavelength for which the X value is closest to one is 514.5 nm. This wavelength is therefore an approximate wavelength for resonance fluorescence. Thus, a polarization analysis of the oxazine perchlorate dye system suggests that most of the singlet emission—and hence the most efficient lasing emission—can be achieved by pumping this dye at around 514.5 nm. The use of a tunable laser would, of course, indicate the most efficient pumping laser line with more precision for this oxazine dye.

Thus, there is provided by the present invention an improved method and apparatus for detecting the wavelength of singlet state resonance fluorescence wherein a sample being analyzed is illuminated sequentially with various incident wavelengths. For each wavelength, linearly polarized and circularly polarized components are allowed to pass sequentially by a first polarizer to the sample. The sample emits light as a result of spontaneous molecular energy transitions. Certain emitted polarized components are then sequentially detected by a detector wherein the intensities of these emitted components can be used to arrive at a new ratio X. The wavelength at which $X=1$ is the wavelength for resonance fluorescence. This technique gives accurate results, and is easy and quick to perform since only a few emission intensity readings need be taken.

Obviously, numerous modifications and variations of the present invention are possible in light of the above teachings. It is therefore to be understood that within the scope of the appended claims, the invention may be practiced otherwise than as specifically described herein.

What is claimed and desired to be secured by Letters Patent of the United States is:

1. A method for detecting the wavelength for singlet state resonance fluorescence of a sample, comprising:
   sequentially illuminating the sample with incident light of different wavelengths, wherein at each wavelength the sample is sequentially illuminated with different components of the incident light, the incident components including a linearly polarized component, and an incident circularly polarized component;
   detecting light emitted from the sample resulting from excitation by the incident light and subsequent spontaneous molecular energy transitions, wherein, for each wavelength of the incident light, intensities of components of the emitted light are sequentially detected, the components of the emitted light including a linearly polarized emitted component, resulting from the incident linearly polarized component, and a circularly polarized emitted component, resulting from the incident circularly polarized component;
   selecting the wavelength at which the intensity of the circularly polarized emitted component is approximately zero and where the intensity of the linearly polarized emitted component has some positive value, the selected wavelength being the wavelength for resonance fluorescence.

2. A method as recited in claim 1, wherein the incident linearly polarized component is polarized in a direction L, and the incident circularly polarized component is polarized in a direction C, and wherein the linearly polarized emitted component includes a first emitted component ($I_\parallel$) being linearly polarized in a direction parallel to L, a second emitted component ($I_\perp$) being linearly polarized in a direction perpendicular to L, and wherein the circularly polarized emitted component includes a third emitted component ($I_{CO}$) being circularly polarized in the same direction as C, and a fourth emitted component ($I_{CTR}$) being circularly polarized in a direction opposite to that of C, wherein $I_\parallel$, $I_\perp$, $I_{CO}$, and $I_{CTR}$ denote the intensities of the various emitted components.

3. The method as recited in claim 2, wherein the selected wavelength is the wavelength at which $$\frac{(I_\| + I_\perp) - (I_{CO} + I_{CTR})}{I_\| + I_\perp + I_{CO} + I_{CTR}}$$

approaches unity.

4. An apparatus for detecting the wavelength for singlet state resonance fluorescence of a sample, comprising:
illumination means for sequentially illuminating a sample with incident light of different wavelengths, the incident light including linearly and circularly polarized components;
first polarizer means for selectively passing only linearly polarized or circularly polarized incident components from said illumination means to the sample;
second polarizer means for selectively passing only linearly polarized or circularly polarized emitted components emitted by the sample;
detector means for detecting the intensity of emitted components emitted from the sample which has passed through said second polarizer means; and
comparator means for comparing said intensities of said linearly polarized emitted components with said intensities of said circularly polarized components.

5. An apparatus for detecting the wavelength of the singlet state resonance fluorescence of a sample as recited in claim 4, further comprising:
control means for automatically controlling the illumination means so as to sequentially generate incident light of different wavelengths, and for controlling the first polarizer means so as to pass only certain components of the incident light from the illumination means, such that at each wavelength, the sample is sequentially illuminated with different components of the incident light, the incident components including a first incident component linearly polarized in a direction L, and a second incident component circularly polarized in a direction C, said control means also acting to control said second polarizer means so as to sequentially pass, for each wavelength of the incident light, components of the emitted light, the components of the emitted light including a first emitted component ($I_\|$) resulting from the incident linearly polarized component, the first emitted component being linearly polarized in a direction parallel to L, a second emitted component ($I_\perp$) resulting from the incident linearly polarized component, the second emitted component being linearly polarized in a direction perpendicular to L, a third emitted ($I_{CO}$) component being circularly polarized in the same direction as C, and a fourth emitted component ($I_{CTR}$) resulting from the incident circularly polarized component, the fourth emitted component being circularly polarized in a direction opposite to that of C, wherein $I_\|$, $I_\perp$, $I_{CO}$, and $I_{CTR}$ denote intensities of the various components; and
said comparator means determines the wavelength for singlet state resonance fluorescence at which $I_{CO} = I_{CTR} = 0$, and $I_\| + I_\perp$ have some positive value.

6. The apparatus as recited in claim 5, wherein said comparator means and said control means both comprise a computer.

7. An apparatus as recited in claim 6, wherein the illumination means is a lasing apparatus.

8. An apparatus as recited in claim 7, wherein the first and second polarizer means each comprise a piezoelectric plate which receives electrical signals from said computer.

9. An apparatus as recited in claim 8, wherein the detector means produces signals proportional to the component intensities, wherein the computer receives said signals from said detector means and computes the solution to the following ratio for each wavelength:

$$\frac{(I_\| + I_\perp) - (I_{CO} + I_{CTR})}{I_\| + I_\perp + I_{CO} + I_{CTR}}.$$

10. An apparatus as recited in 9 wherein said computer compares ratios obtained, wherein the ratio having an absolute value closest to the value one is selected, said ratio corresponding to an approximate wavelength for singlet state resonance fluorescence.

11. A method of detecting the wavelength for singlet state resonance fluorescence of a sample comprising the steps of:
sequentially illuminating the sample with incident light of different wavelengths. wherein at each wavelength the sample is sequentially illuminated with different components of the incident light, the incident components including a first incident component linearly polarized in a direction L, and a second incident component circularly polarized in a direction C;
detecting light emitted from the sample resulting from excitation by the incident light and subsequent spontaneous molecular energy transitions, wherein, for each wavelength of the incident light, intensities of components of the emitted light are sequentially detected, the components of the emitted light including a first emitted component ($I_\|$) resulting from the incident linearly polarized component, the first emitted component being linearly polarized in a direction parallel to L, a second emitted component ($I_\perp$) resulting from the incident linearly polarized component, the second emitted component being linearly polarized in a direction perpendicular to L, a third emitted component ($I_{CO}$) resulting from the incident circularly polarized component, the third emitted component being circularly polarized in the same direction as C, and a fourth emitted component ($I_{CTR}$) resulting from the incident circularly polarized component, the fourth emitted component being circularly polarized in a direction opposite to that of C, wherein $I_\|$, $I_\perp$, $I_{CO}$, and $I_{CTR}$ denote intensities of the various emitted components: and
selecting the wavelength at which $I_{CO} = I_{CTR} = 0$, and $I_\| + I_\perp$ have some positive value, the selected wavelength being the wavelength for resonance fluorescence.

* * * * *